US010945702B2

(12) United States Patent
Palanisamy et al.

(10) Patent No.: US 10,945,702 B2
(45) Date of Patent: Mar. 16, 2021

(54) DOPPLER ULTRASOUND SYSTEM FOR DIAGNOSING CAROTID STENOSIS

(71) Applicant: KONINKLIJKE PHILIPS N.V., Eindhoven (NL)

(72) Inventors: Krishnamoorthy Palanisamy, Bangalore (IN); Sushanth Govinahallisathyanarayana, Bangalore (IN); Rajendra Singh Sisodia, Bangalore (IN); Nagaraju Bussa, Bangalore (IN); Shankar Mosur Venkatesan, Bangalore (IN); Shriram Sethuraman, Cambridge, MA (US); John Petruzzello, Carmel, NY (US); Ajay Anand, Fishkill, NY (US); Shiwei Zhou, Yorktown Heights, NY (US); Ramon Quido Erkamp, Yorktown Heights, NY (US); Vikram Basawaraj Patil Okaly, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1329 days.

(21) Appl. No.: 14/906,966

(22) PCT Filed: Jul. 2, 2014

(86) PCT No.: PCT/IB2014/062790
§ 371 (c)(1),
(2) Date: Jan. 22, 2016

(87) PCT Pub. No.: WO2015/011585
PCT Pub. Date: Jan. 29, 2015

(65) Prior Publication Data

US 2016/0157814 A1 Jun. 9, 2016

Related U.S. Application Data

(60) Provisional application No. 61/857,837, filed on Jul. 24, 2013.

(51) Int. Cl.
*A61B 8/06* (2006.01)
*A61B 8/08* (2006.01)
*A61B 8/00* (2006.01)

(52) U.S. Cl.
CPC .............. *A61B 8/06* (2013.01); *A61B 8/0891* (2013.01); *A61B 8/4483* (2013.01); *A61B 8/483* (2013.01); *A61B 8/488* (2013.01); *A61B 8/5223* (2013.01)

(58) Field of Classification Search
CPC .......... A61B 8/488; A61B 8/06; A61B 8/0891
See application file for complete search history.

(56) References Cited

U.S. PATENT DOCUMENTS 5,474,073 A * 12/1995 Schwartz ................ A61B 8/14 128/916
5,891,039 A * 4/1999 Bonnefous ............... A61B 8/13 600/454

(Continued)

FOREIGN PATENT DOCUMENTS

WO 2002069805 A1 9/2002
WO 2010089660 A1 8/2010

(Continued)

OTHER PUBLICATIONS

Taylor, Fiona C., Stroke in India, South Asia Network for Chronic Disease, 2009.

(Continued)

*Primary Examiner* — Luther Behringer

(57) ABSTRACT

A diagnostic ultrasound system for carotid artery diagnosis has a two dimensional array probe with a low element count and relatively large element size which can cover an area of the carotid artery at its bifurcation. The elements are operated independently with no phasing, and detect Doppler flow spatially beneath each element. The system produces maps of carotid blood flow in two or three dimensions and can (Continued)

assemble an extended view of the flow by matching segments of the carotid flow as the probe is moved over the vessel. Once the carotid artery has been localized, the degree of stenosis is assessed by automated measurements of peak systolic velocity and blood flow turbulence.

19 Claims, 7 Drawing Sheets

(56) References Cited

U.S. PATENT DOCUMENTS 6,102,865 A * 8/2000 Hossack ................ A61B 8/145 600/443
6,261,233 B1 7/2001 Kantorovich
6,524,249 B2 * 2/2003 Moehring ................ A61B 8/06 600/438
6,730,030 B2 * 5/2004 Palti ......................... A61B 8/06 600/441
6,815,694 B2 * 11/2004 Sfez ..................... A61B 5/0073 250/492.1
7,285,094 B2 * 10/2007 Nohara ............... G01S 7/52047 600/447
8,388,544 B2 3/2013 Hoctor et al.
9,579,078 B2 * 2/2017 Anand ................ G01S 15/8927
9,788,813 B2 * 10/2017 Adam ...................... A61B 8/12
10,231,694 B2 * 3/2019 Vajinepalli ............... A61B 8/06
2002/0091319 A1 * 7/2002 Moehring ................ A61B 8/06 600/454
2002/0151795 A1 * 10/2002 Palti ......................... A61B 8/06 600/454
2003/0163046 A1 * 8/2003 Nohara ............... G01S 7/52047 600/443
2004/0099815 A1 * 5/2004 Sfez ..................... A61B 5/0073 250/492.1
2005/0119573 A1 6/2005 Vilenkin
2009/0292208 A1 * 11/2009 Jeffrey, Jr. .......... G01S 15/8927 600/454
2012/0095347 A1 * 4/2012 Adam ...................... A61B 8/12 600/459
2013/0138095 A1 5/2013 Gertner
2014/0243673 A1 * 8/2014 Anand ................ G01S 15/8927 600/447
2014/0343431 A1 * 11/2014 Vajinepalli ............... A61B 8/06 600/454
2014/0358000 A1 * 12/2014 Gupta .................... A61B 8/466 600/441

FOREIGN PATENT DOCUMENTS

WO 2013001503 A2 1/2013
WO 2013088320 A1 6/2013
WO 2015011594 A1 1/2015

OTHER PUBLICATIONS

Pandian, Jeyaraj D. et al "Stroke", American Stroke Association, vol. 38, pp. 3063-3069, 2007.

* cited by examiner

DOPPLER ULTRASOUND SYSTEM FOR DIAGNOSING CAROTID STENOSIS

CROSS-REFERENCE TO PRIOR APPLICATIONS

This application is the U.S. National Phase application under 35 U.S.C. § 371 of International Application No. PCT/IB2014/062790, filed on Jul. 2, 2014, which claims the benefit of U.S. Provisional Patent Application No. 61/857,837, filed on Jul. 24, 2013. These applications are hereby incorporated by reference herein.

This invention relates to medical diagnostic ultrasound systems and, in particular, to a Doppler probe system for automated screening of carotid stenosis.

Stroke is the third leading cause of death world-wide. According to the World Health Organization, stroke accounted for more than 5.5 million deaths in 2002 with about 50% of those deaths occurring in China and India. Although the incidence is declining in developed countries, stroke nevertheless accounts for a mortality of 163,000 in the United States. A significant portion of these deaths are believed to be a result of disease in the carotid bifurcation. The carotid artery bifurcation, where the common carotid artery (CCA) branches into the internal (ICA) and external (ECA) carotid arteries, is a common site of atherosclerotic disease. Stenosis or narrowing of the ICA, the branch which supplies blood to the brain, has long been known to be related to the incidence of ischemic stroke. The use of the severity of carotid stenosis has evolved as a surrogate measure of the risk of stroke.

The incidence of carotid atherosclerosis and mortality associated with stroke is an increasing problem in the developing world. In these countries, a carotid artery screening device that can be used in low resource settings would address this growing problem by offering several features. First, there is often a lack of skilled personnel in these settings, and so the device should be able to be used with minimal training and instruction. Second, the device should be inexpensive so as to be affordable in these settings. Third, the device should be able to classify the degree of stenosis in the carotid arteries in a highly automated way without the use of high-end duplex ultrasound scanners that may not be available in the rural setting.

In accordance with the principles of the present invention, a diagnostic ultrasound system for carotid artery diagnosis includes a simple, Doppler ultrasound probe. The probe has a two dimensional array of transducer elements with a low count of elements of relatively large size which can cover an area of the carotid artery at its bifurcation. The large sized elements are operated independently with no phasing, thereby reducing the cost of the Doppler system. The probe and system of the present invention can produce a representation of carotid blood flow in two or three dimensions and can assemble an extended view of the flow by matching segments of the carotid flow as the probe is moved over the vessel. Once the carotid artery has been localized, the degree of stenosis is assessed by automated measurements of peak systolic velocity and blood flow turbulence.

Figure 2A:
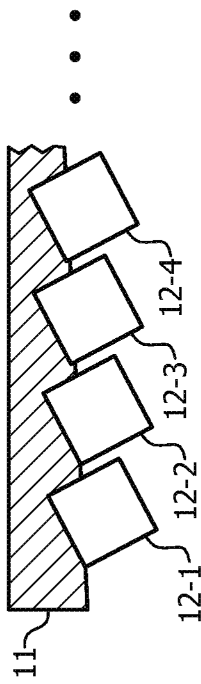
FIG. 2 illustrates the size and dimensions of the elements of an array transducer of a probe of the present invention.
Figure 2:
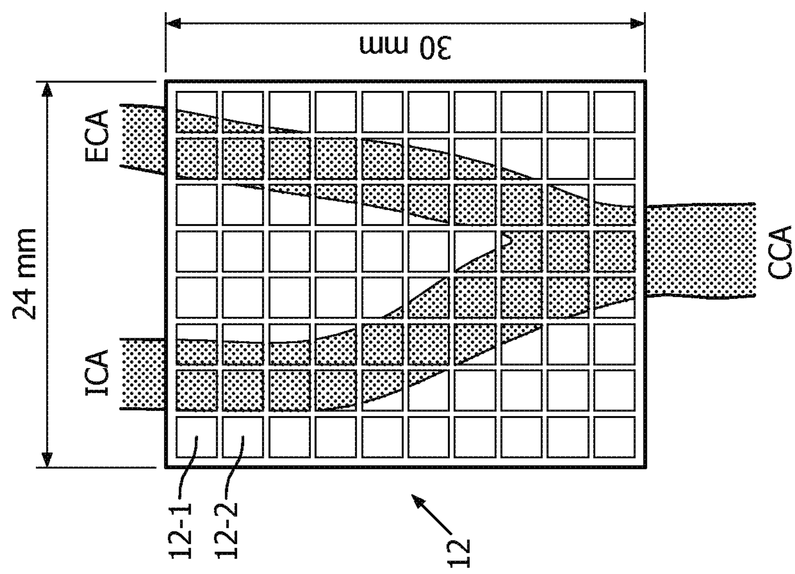

FIG. 2*a* illustrates the angling of the transducer elements of the array of FIG. 2 for good Doppler reception.

Figure 3:
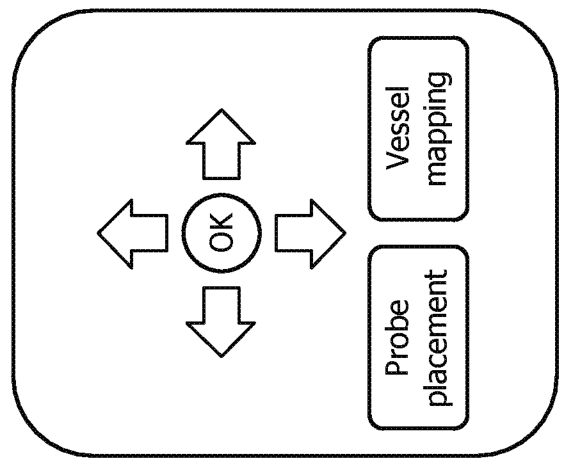

FIG. 3 illustrates a probe placement display of an ultrasound system of the present invention which guides an operator in proper probe placement over the carotid artery.

Figure 4:
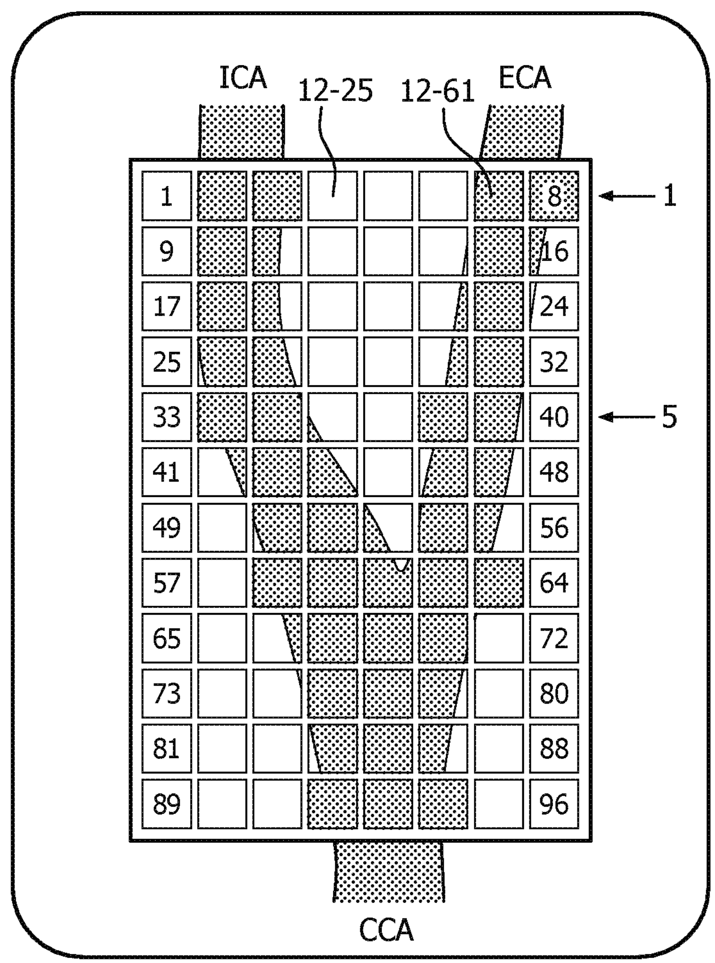

FIG. 4 illustrates the operation of a Doppler probe of the present invention in discrete rows of elements.

Figure 5:
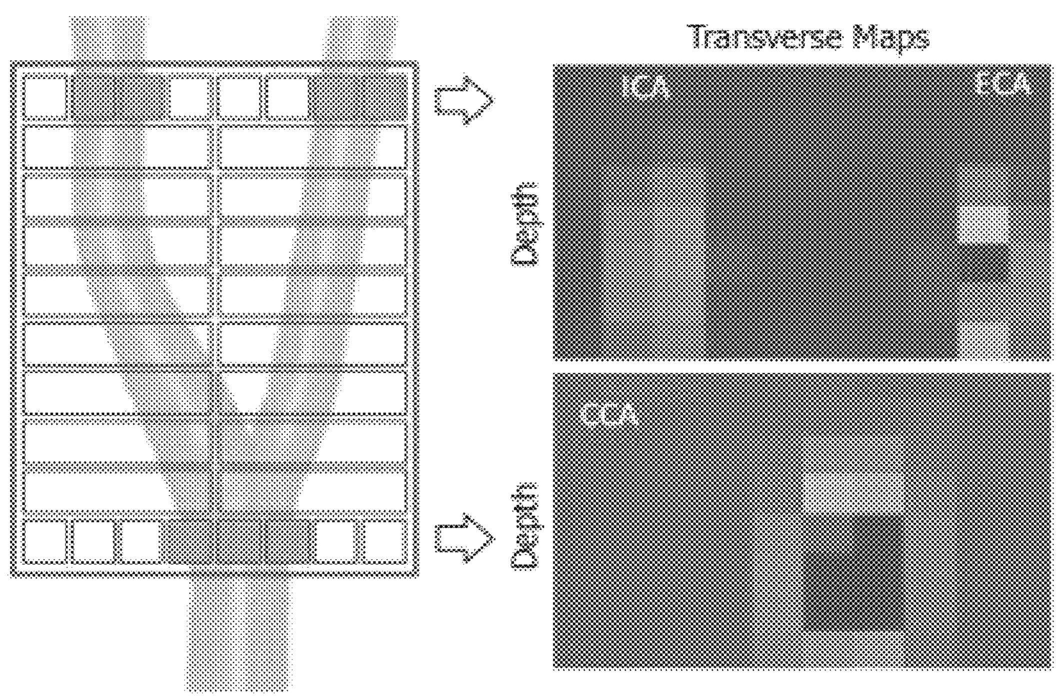

FIG. 5 illustrates a two dimensional vessel map produced by an ultrasound system of the present invention.

Figure 6:
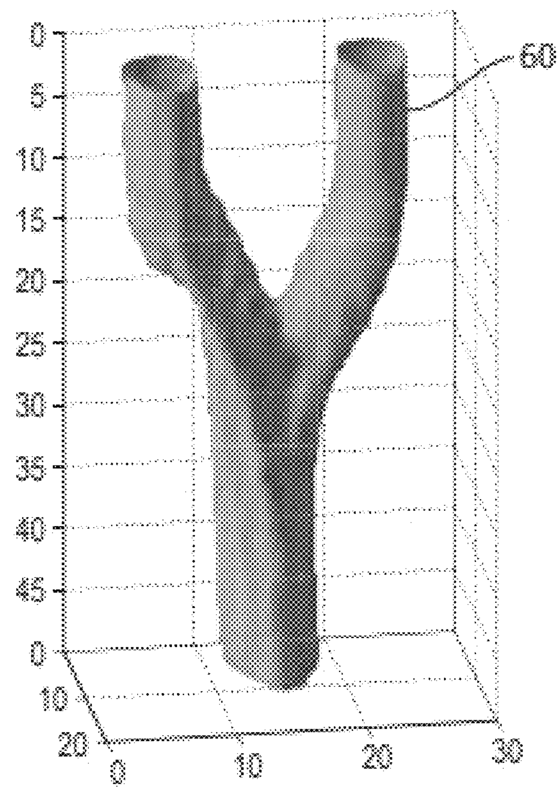
Figure 7A:
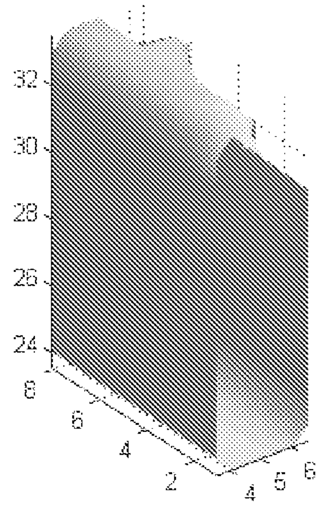
Figure 7B:
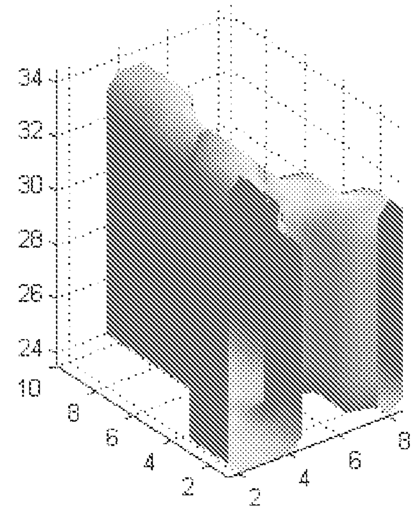
Figure 7C:
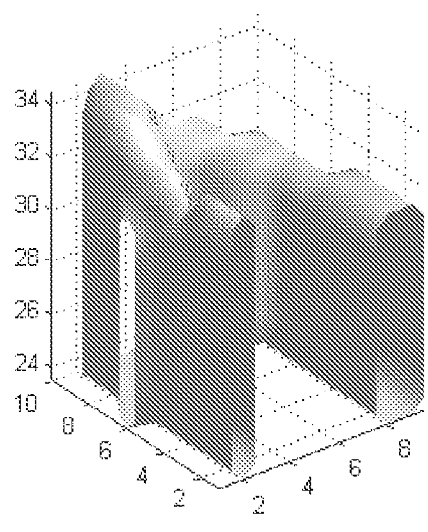
Figure 7D:
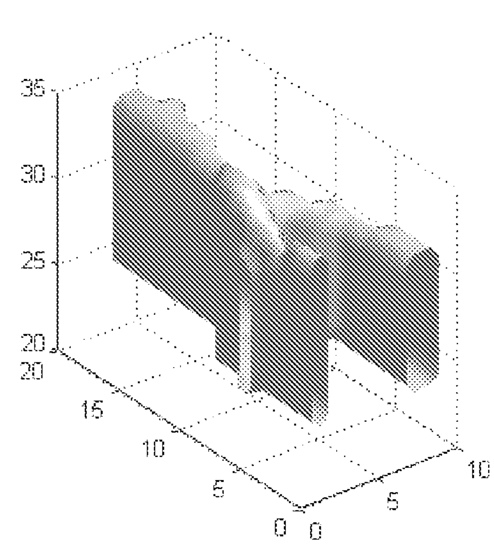

FIG. 6 illustrates a three dimensional vessel map produced by an ultrasound system of the present invention.

FIGS. 7*a*-7*d* illustrate the progressive assembly of a three dimensional vessel map produce by scanning with a probe and system of the present invention.

Figure 8:
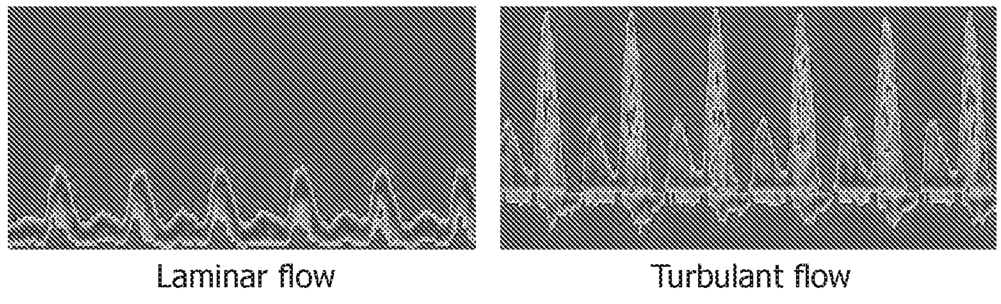

FIG. 8 illustrates spectral Doppler displays of flow conditions encountered in the carotid artery.

Figure 9:
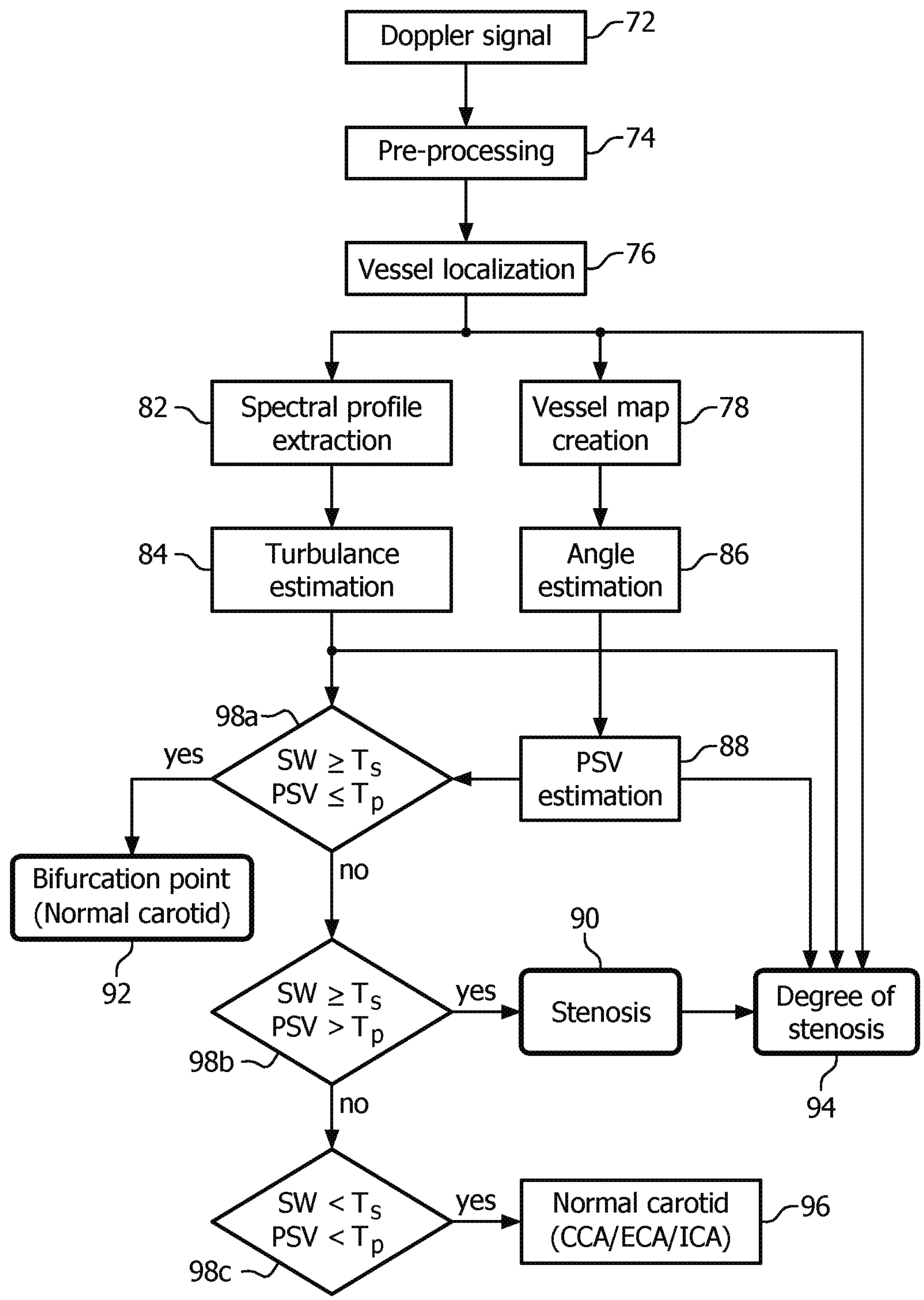

FIG. 9 is a flow chart of the automated assessment of turbulence and peak systolic velocity in a system of the present invention.

Figure 10:
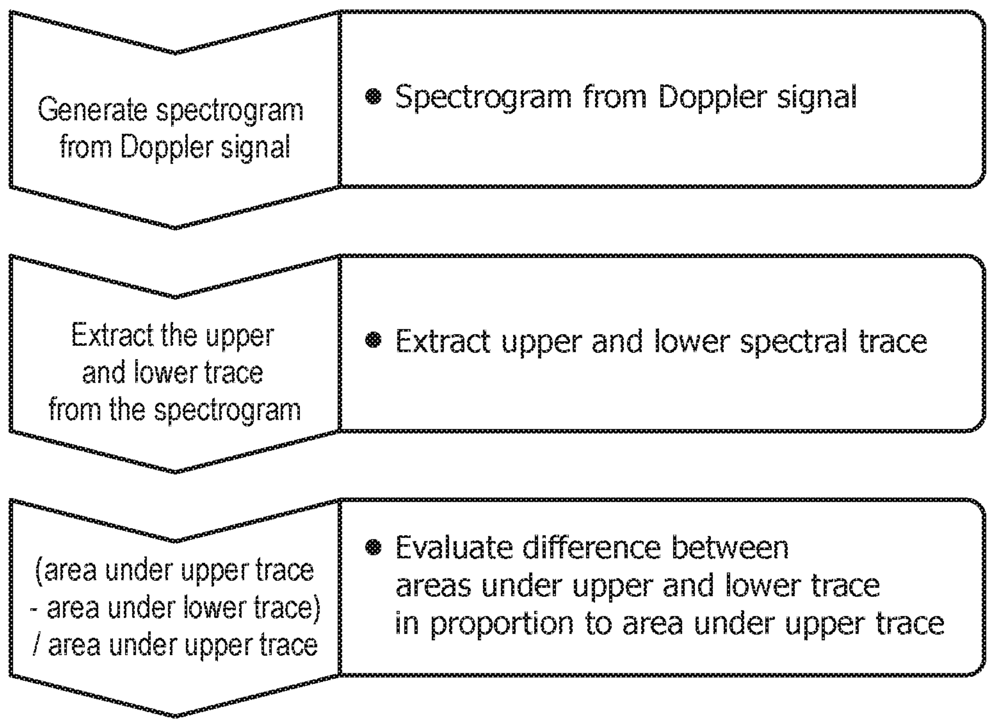

FIG. 10 is a diagram of the basic steps of flow analysis in accordance with the present invention.

Figure 11:
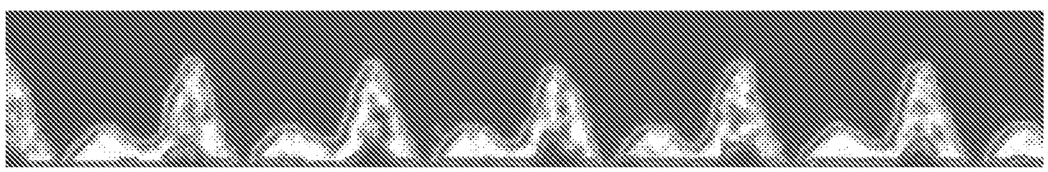

FIG. 11 illustrates a Doppler spectrum with the upper and lower extremes of its envelope traced.

Figure 1:
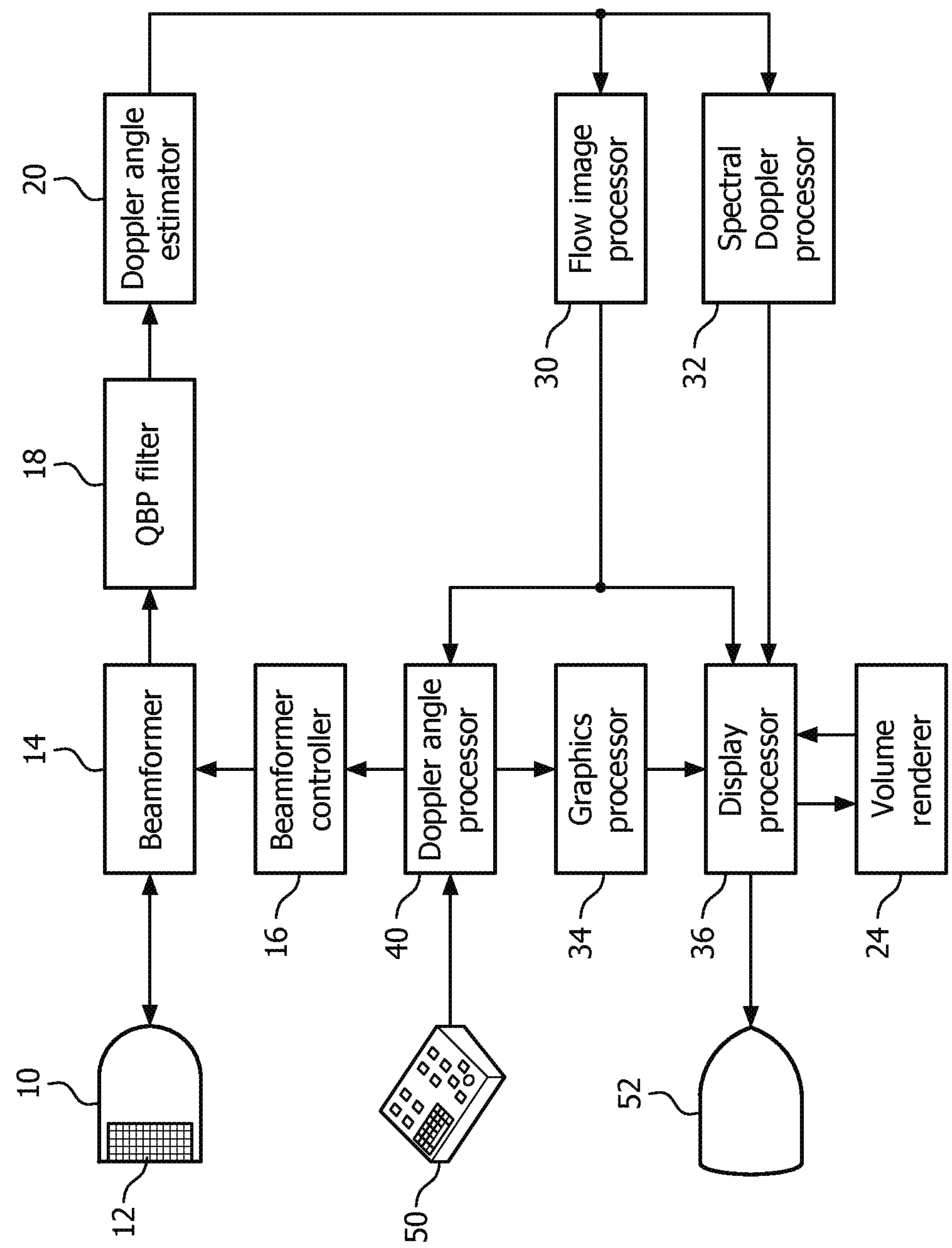
FIG. 1 illustrates in block diagram form an ultrasound system constructed in accordance with the principles of the present invention.

Referring first to FIG. 1, an ultrasound system constructed in accordance with the principles of the present invention is shown in block diagram form. An ultrasound probe 10 contains a transducer array 12 of transducer elements which transmit ultrasound waves into the body and receive returning echo signals for Doppler processing. Control and timing of ultrasound transmission and reception is provided by a beamformer controller 16 which controls system beamformer 14. The beamformer 14 is not a conventional delay-and-sum beamformer as the transducer array is not operated in a phased manner. Instead, each element is separately actuated to transmit ultrasound waves directly into the body from its front surface and receive reflections from the waves individually. The beamformer controls the timing of successive transmit-receive intervals (the pulse repetition interval or PRI) by each transducer so that an ensemble of temporally spaced echoes is received by each transducer element at successive depths over a depth range of interest, which is the nominal depth at which the carotid artery is located. Each ensemble of echo samples can then be Doppler processed to detect the flow condition in front of every transducer element. A quadrature bandpass filter 18 processes the echo signals into quadrature I and Q components. The separate components are used by a Doppler angle estimator 20 to estimate the phase or frequency shift of a Doppler signal at the depths in front of each transducer element where Doppler interrogation is to be performed. Alternatively Doppler power may be estimated. The Doppler frequencies or intensities at depths in front of each transducer which are produced by the Doppler angle estimator 20 can be mapped directly to velocity values of flow or Doppler power at those depth locations. This Doppler data is coupled to a flow image processor 30 which spatially processes the data into a two or three dimensional image format, in which the velocity values are color- or intensity-coded. This spatial Doppler vessel map is processed by a display processor 36 and displayed on display 52 to illustrate the locations in the anatomy beneath the array transducer where flow is taking place and the velocity and direction of that flow by the color coding or Doppler power by intensity modulation. Doppler data is also coupled to a spectral Doppler processor 32 which produces a spectral analysis of the Doppler data for peak systolic velocity and turbulence analysis as described below. A Doppler angle processor 40 conditions the process for the angle of Doppler interrogation which is preferably set by inclining the direction of wave transmission by the transducer elements as described below. A graphics processor 34 is provided to overlay vessel map coordinates and other graphical data such as patient name on the displayed image. A volume renderer 24 performs volume rendering of three dimensional vessel map data for the production of three dimensional vessel maps as described below. The entire system is operated by user controls 50.

FIG. 2 illustrates a transducer array 12 for a probe 10 of the present invention. This embodiment is an array for a probe with a total of 80 elements, each measuring 3 mm by 3 mm arranged in a two dimensional matrix containing 10 rows by 8 columns. In such a configuration, the area of coverage is 30 mm by 24 mm. Transducer arrays with this small number of elements and elements of this relatively large individual size are easier to dice than fine-pitched array elements, making this array simple to fabricate with high yields and hence relatively inexpensive to make. The factors to consider in selecting the number of element include coverage, resolution, and a number which provides acceptable accuracy as compared to a standard ultrasound probe. Element sizes ranging from 3 mm by 3 mm to 6 mm by 6 mm have been found to be acceptable for unfocused elements used with nominal depths of the carotid artery. An array size of around 40 mm has been found suitable for covering the branches of the carotid artery. As FIG. 2 illustrates, the probe is intended to be placed against the neck of a patient over the carotid artery. When the probe aperture is longitudinally in line with the carotid artery and the bifurcation of the artery is within the field of view, the transducer will cover an appreciable area of the carotid artery with the common carotid artery (CCA) at one end and the internal (ICA) and external (ECA) branches at the other end. The elements in the probe are placed at an angle to provide a Doppler angle of 30-60 degrees. As is well known, no Doppler signal can be obtained when the direction of blood flow is orthogonal to the direction of the ultrasound waves, and maximal signals are obtained when the wave are directed in line with the flow. Thus, if the elements of the array 12 were aimed straight into the body, little or no Doppler signals would be realized from the carotid flow immediately beneath the array. To account for this directional sensitivity the elements of the array 12 are angled at an angle of 30-60 degrees away from normal as illustrated in FIG. 2*a*. A tilt of around 30 degrees has been found to yield acceptable results. Additional angulation can be provided by tilting the probe in relation to the skin surface during scanning. This drawing shows the end elements 12-1, 12-2, 12-3 and 12-4 of the first four rows of elements canted at the selected Doppler angle and retained in position by an overlying layer of transducer lens material layer 11 which is generally a polymeric rubber-like material such as Room Temperature Vulcanizing silicone (RTV). The thickness of the RTV lens can be uniform across the array transducer, or can be tapered in thickness to provide some or all of the tilt for setting the nominal Doppler angle. The Doppler angle at which the elements are angled can be entered into the ultrasound system automatically from the probe's personality chip or manually from the user controls to condition the system to account for the proper angle correction to be used for the Doppler angle of the probe elements. The system may desirably also include a Doppler angle feedback indicator controlled by an algorithm that processes the strength of the Doppler return signals and detects unfavorable Doppler angles, which suggests that the user manually reposition the probe at a more favorable angle.

The elements of the array transducer are excited with excitation pulses to work in the pulsed wave mode. In the pulsed wave mode, it is possible to provide depth resolution of the Doppler signals. For instance, an element size of 3 mm by 3 mm generally provides enough resolution to sample and obtain the velocity in a narrow region of the high speed jet produced in carotid arteries with stenosis. The elements of the non-phased transducer array 12 are fired simultaneously or independently in a customizable firing sequence under control by the beamformer 14.

Operation of a probe and system of the present invention proceeds as follows. A sequence of elements (a small sub-section of the entire probe) is fired simultaneously. The sample volume for Doppler flow interrogation in front of each element is increased sequentially to cover a range of depths. In the embodiment of FIG. 4, in which the probe contains an array of 96 elements, 4 rows could be activated simultaneously, e.g., rows #1, #5, #8 and #12 as shown in this drawing. The Doppler spectrum is acquired continuously from each of the 8 elements in each of these rows. After at least 3 cycles of Doppler flow data are acquired, the flow image processor 30 computes a sum-plot (integration of Doppler power in a specified frequency band, e.g. 300 Hz to 1500 Hz). The magnitudes of the sum-plot values enable the elements that are directly above the vessel to be identified. For instance, transducer element 12-25 is not over a portion of the carotid artery and will sense no flow (will produce a negligible power Doppler signal.) Transducer element 12-61, on the other hand, is directly above the carotid artery and will produce a significant power Doppler signal. The flow image processor 30 can then produce a grid-like map of the location and position of the carotid artery branches beneath the probe as indicated in FIGS. 4 and 5. Each box in an 8 by 12 display grid is filled in with a brightness or color when a significant Doppler signal is detected by a corresponding transducer element, and is not illuminated when substantially no Doppler signal is detected. In FIG. 4, for instance, the third, fourth, seventh and eighth boxes in the first row of the grid are illuminated in response to the detection of flow in the ICA and ECA by those elements in that row which are over those carotid branches. A similar result is obtained from elements 34, 35, 38 and 39 in row 5. Boxes corresponding to elements 59-63 of row 8 are illuminated because they detected flow in the CCA below the carotid bifurcation, as is also the case for boxes corresponding to elements 92-94 in row 12. As FIG. 4 illustrates, this will present a simple two dimensional grid vessel map of the flow in the carotid artery beneath the array transducer. A similar result can also be obtained in the depth dimension as shown in FIG. 5. This shows the results from depth-gating the Doppler signal samples from six discrete depths below the elements in the top and bottom rows of the array 12. The transverse maps to the right of the array illustration shows faintly illuminated blocks at six depths where the second, third, seventh and eighth elements in the top row have detected flow in the ICA and the ECA. The lower map shows a wider, more illuminated set of depth blocks where the center three elements of the bottom row of elements have detected the stronger flow in the CCA which is beneath that row of elements. The values of these vertical depth block in each column can be combined in various ways to obtain a display value for a box in the longitudinal display shown to the left of the transverse maps, if desired.

An object of an implementation of the present invention is to provide real-time feedback to the user such that the user is guided in placing the probe on the neck so that it covers the bifurcation of the carotid artery. Since this is a non-image based system, feedback can be given to the user through a set of indicators on the screen that guides the user to move the probe in the appropriate direction. In this example, the ideal placement of the probe is when the flow image detector detects a single vessel branch (CCA) at rows 8 & 12 of the grid display and two separate vessel branches (ICA and ECA) in rows 1 & 5 of the grid as shown in FIG. 4. The elements in these rows are continuously fired and the flow image processor computes the accumulated Doppler power of the signals received by each element in real time. The grid blocks which are illuminated in response to significant Doppler signal returns inform the system of the placement adjustment needed to obtain good probe placement. If the placement is good, the "OK" indicator is highlighted in the probe guidance display of FIG. 3. If not, appropriate one of the arrows in the guidance display are highlighted to guide the user in probe placement. An optimal positioning of the probe is achieved when the display grid showing the depth accumulated Doppler power (FIG. 4) indicates a separation of the vessel segments in the carotid bifurcation. The "Probe placement" and "Vessel Mapping" display buttons at the bottom of the guidance display tell the user the current mode of operation, either probe placement or vessel mapping. If the user is in the Vessel Mapping mode and wants to readjust the positioning of the probe over the carotid artery, the user taps the Probe placement display button to return the system to that mode and the Probe placement button responds by illuminating. Since approximately 3 seconds worth of Doppler data is required for a single iteration, a guidance indication can be determined and updated in a time of 3 seconds. The maximum time to achieve acceptable placement of the probe over the carotid artery depends on the number of iterations required to successfully place the probe in the proper position for carotid artery stenosis detection.

Once the probe is placed, the next step is to obtain ultrasound Doppler data from all the elements in the probe array and map the vessels in accordance with the elements which detect flow. The accumulated Doppler power is computed as described above in conjunction with FIG. 5 for the depths of interest to generate a 3D representation of the carotid vessels. The 3D representation is produced from the depth values detected by all of the elements and processed by the volume renderer 24 into a 3D display map. As shown in FIG. 6, a 3D display map 60 of the bifurcated vessel is displayed.

Following vessel mapping in either two (FIG. 4) or three (FIG. 6) dimensions, Doppler data is acquired from all of the elements to extract the peak systolic velocity which can aid in classification of a stenosis. Additionally if desired a Doppler spectrum can be extracted at a suspected point of stenosis to further aid the diagnosis as described below.

When the probe 10 has a small aperture, it may not be possible to acquire a sufficiently sized portion of the carotid, its branches and bifurcation in a single acquisition. In such a case multiple volume acquisition is employed to acquire segments of the carotid artery in sub-areas or sub-volumes by movement of the probe along the neck, then stitching the smaller segments together to form the desired vessel map. Manual movement of probe implies that there is no calibration, the overlap region may vary among two consecutive acquisitions, and there is also potential variation in the angle and quality of signal acquisition. Thus, instead of all the data being acquired in one volume, data is acquired in multiple sub-volumes to cover the entire carotid anatomy. From the multiple acquisitions, the carotid vascular anatomy must be reconstructed to verify if the entire carotid anatomy was scanned, and so the sub-volumes must be stitched together. This is done by "stitching" together successively acquired, spatially different but overlapping subvolumes by aligning their matching data in the overlapping region. The overlapping region of each subvolume is determined from a match of the time domain Doppler obtained from the individual transducer elements. As a simple example, one subvolume may have a column of voxels with flow velocity values of 0, 3, 5, 3, and 0 cm/sec. When a matching column of voxels in an overlapping subvolume is found with the same or similar Doppler values, the subvolumes are aligned on the basis of this identity of sequential voxel values. Other Doppler spectral characteristic instead of or in addition to velocity can be used to make the match. This stitching is performed purely based on the signal characteristics because relative position of the probe with reference to the neck is not easy to obtain.

Accurate vessel stitching is essential in order to reconstruct the vascular anatomy to estimate the angle of insonation across multiple volumes at one sweep of the probe. This enables the determination of peak systolic velocity across the anatomy. Peak systolic velocity is a clinically accepted diagnostic indicator to grade stenosis according to the following consensus criteria:

| Degree of stenosis | PSV (cm/s) |
|---|---|
| Normal or <50% | <125 |
| 50%-69% | 125-230 |
| >70% | >230 |
| Total occlusion | No flow |

In embodiments of the present invention, it is difficult for the user to understand how much of the artery cluster under investigation has been covered by a sweep of the probe. It is difficult to interpret from the reconstruction of any of the typical sampled sub-volumes, e.g., (a) (b) or (c) of FIG. 7, whether the artery structure has been covered with anatomical cues from a single volume. Therefore, the data from multiple volumes is stitched together to completely reconstruct the vascular anatomy and provide an anatomical basis for artery identification. Anatomical cues from the generated vessel map of the sub-volumes are used as well as signal characteristics to complete the vascular anatomy reconstruction. When the Doppler signal is of sufficient signal to noise ratio to obtain a complete anatomical reconstruction in pulsatile flow, and the probe is moved uniformly over the artery structure under investigation, the following steps may be employed in accordance with the present invention to reconstruct the full anatomy. First, the probe 10 is placed in a first location resulting in acquisition of a first sample volume. The probe is manually moved to a second location, adjacent to the first location such that a resulting new acquisition sample volume is partially overlapped with the first sample volume. Each volume in this example is a three dimensional matrix containing returned ultrasound echo data. Next, further sample volumes are acquired in the same manner, such that the vessel structure of interest is fully covered. In this approach, it may not be feasible to know the completion of vessel map reconstruction until the end of the process.

Next, for each volume, a signal in the volume is identified by highlighting the different segments in the 3D space of the vessel as shown in FIGS. 7*a*-7*d*. Vessel map identification is used to identify a vessel segment in a given volume. A list of unique vessel segments is identified using the previous step. The number of vessel segments is compared among the sample volumes. This helps to clearly identify the region of overlap in the sample volume where the number of regions is non uniform, such as the volume containing the bifurcation point of the carotid artery, using anatomical information from the reconstruction. It also gives an indication of where to search for matching signal data, e.g., the overlap between FIG. 7(*b*) and FIG. 7(*c*) can only be where there are two distinct vessels in FIG. 7(*b*).

The data of all the good spectra from the top most row of each column of one sample volume is extracted in order, and correlated with the data of each of the rows of the subsequent (adjacent) volume. Let k be a row in which a spike in correlation occurs. The spike in correlation at row k indicates that all the data from row k to the last row of the probe are in the overlapping region. Since the effects of noise are unpredictable on the signal, it may happen that one of the acquisitions of the overlapping volumes is more contaminated by noise than the other. In this case, the overlapping area is assigned to the volume where this area has more analyzable spectra. In the event that the number of such spectra is equal, the overlapping region can be assigned to either volume.

Let there be p rows matching the anatomical cues (or number of regions in the slice). Let the signals of each transducer on these p rows at all depths showing pulsatile flow (signal from blood flow) be $T_{ij}$. Let the pulsatile signal of the ith row of transducers be $R_i$:

$$R_i=\Sigma_{j=1}^{c}T_{ij} \quad \text{(i)}$$

where c is the number of columns. The matrix of row signals RM is obtained as:

$$RM=\{R_1\ R_2\ R_3\ \ldots\ R_k\ \ldots\ R_p\} \quad \text{(ii)}$$

Let the signal on the first row of the previous volume be FS:

$$FS=\Sigma_{j=1}^{c}T_{1j} \quad \text{(iii)}$$

where c is the number of columns. The start of the overlap region is obtained by cross-correlating the row signal matrix with FS as follows:

$$CV = CrossCorr\ (RM,\ FS) \quad \text{(iv)}$$

$$CV = \sum_{n=-inf}^{inf} RM(i+n)'FS(k)$$

Where $$RM(i+k)$$

is $$\begin{bmatrix} R_1(i+k) \\ R_2(i+k) \\ R_3(i+k) \\ \vdots \\ R_p(i+k) \end{bmatrix}$$

CV is the vector of cross correlations $$k=\text{Max}(|(CV)|) \quad \text{(v)}$$

and $R_k$ is the row corresponding to index k. Since the direction of motion is assumed to be uniform and correlation is performed to find the start of the overlapping region we know that $R_k$ to $R_p$ is the overlapping region. Volume data from $R_k$ to $R_p$ is assigned to the corresponding volume. This yields the volumes to be stitched as $S_1$, $S_2$ and $S_3$. The volumes to be stitched are stacked in the direction of motion and connected by interpolation and/or smoothing.

Blood flow in the carotid artery can be laminar or turbulent. Laminar flow is uniform, with all blood cells moving at relatively the same speed and in the same direction. Turbulent flow is characterized by random chaotic swirling, in which blood cells within the vessel are moving in many directions but typically have a net forward flow. Doppler spectra of laminar flow appear as broadening of the spectral line and filling of the spectral window. A turbulent flow pattern appears as spectral broadening with components below the baseline. Spectral broadening is a term applied to waveform alterations that are representative of turbulent flow. It is defined as the increased distribution of the frequencies present in a Doppler spectrum as illustrated by the Doppler flow spectrograms of FIG. 8. In the carotid artery, this type of turbulence is present at the bifurcation point (i.e., the carotid bulb, equivalent from the point of view of flow characteristics) and at a narrowing or stenosis of the vessel.

The main way of distinguishing these two cases of turbulence is through the measurement of the peak systolic velocity (PSV). The presence of stenosis is usually characterized by an elevated PSV accompanying turbulence. The criteria for dangerous levels of plaque are generally related to percentage of stenosis; also, the degree of stenosis is determined by the peak velocity of the blood as follows:

| Degree of stenosis | PSV (cm/s) | Turbulence (Spectral Broadening) |
|---|---|---|
| Normal | <125 | Normal & High at carotid bulb |
| <50% | <125 | High |
| 50%-69% | 125-230 | High |
| >70% | >230 | High |
| Total occlusion | No flow | Nil |

Detecting the Doppler shift caused by increased velocity can determine whether there is dangerous plaque present.

Distinguishing the characteristics of the bifurcation of the carotid artery from the characteristics of a stenosis can be done as follows:

| Condition/Feature | PSV | Turbulence (Spectral Broadening) |
|---|---|---|
| Bifurcations (Carotid bulb) | Normal | High |
| Stenosis | High | High |

This relationship shows that by estimating the turbulence in terms of spectral broadening and the PSV one can easily identify the segments of interest (like bifurcation and a stenosis jet) with the help of suitable thresholds for PSV and spectral broadening. The present invention uses this information to detect the segments of interest without any imaging of the carotid artery. Further, the present invention provides an automated method to characterize the turbulence present in the carotid cluster with differentiated degrees of stenosis. Experimental results have shown this estimation of stenosis in a segment of interest, together with a combination of turbulence with peak systolic velocity, provide a robust technique for evaluating stenosis.

Spectral Doppler ultrasound velocimetry involves the systematic analysis of the spectrum of frequencies that constitute the Doppler signal. The Doppler signal obtained for clinical use is composed of a range of frequencies with varying amplitude content. Therefore, systematic processing is required before the Doppler shift frequencies are computed. The systematic process of FIG. 9 estimates the two most important parameters to be estimated for stenosis evaluation, the PSV and turbulence.

In block 72 Doppler signals are acquired from the volumetric region of the carotid artery as described above and the Doppler signals is pre-processed (74) to remove unwanted noisy signal components. The vessel localization step 76 identifies whether the acquired Doppler signals contain vessel information (CCA, ICA, ECA or bifurcation point) or not. This is done with the help of a predefined power threshold for the Doppler power. The power in the time domain (the sum of the square of all the values divided by signal length) is computed for all of the sample volumes of the carotid artery. Then the average power is computed from all the sample volumes. Finally the sample volume that exhibits the highest power above the average value is considered as a segment having vessel information.

The spectral profile extraction at step 82 involves two steps: (i) computing a spectrogram using the spectral Doppler processor 32 and (ii) processing the spectrogram (smoothing, thresholding, noise removal, etc.) to obtain a good spectral profile. The spectrogram is obtained using a Fast Fourier Transform (FFT) based power spectrum with a 20 millisecond Hamming window using 256 data points and 50% overlap. After this a smooth and reproducible maximum frequency envelope is extracted from the generated spectrogram. To obtain a high quality maximum frequency envelop a first order Infinite Impulse Response (IIR) filter is initially applied to the obtained spectrogram. Next, a 2D median filter is applied to the pulse waveform obtained from the IIR filter. The output of the median filter is used to extract the spectral frequency envelope.

To estimate PSV in step 88, first a 3D vessel map is created in step 78 from the identified vessel information as described previously. From the vessel map the Doppler angle is estimated in step 86 by piecewise linear fit of the geometrical centroids of the carotid vessel structure obtained from the vessel map. The maximum Doppler shift frequency is also computed from the estimated spectral profile.

The peak systolic velocity is estimated in step 88 from the Doppler angle and the maximum Doppler shift using the standard Doppler equation $$v=(F_s \times c)/(2 \times F_t \times \cos\theta),$$

where $F_s$ is the Doppler frequency shift, c is the speed of sound in body (assumed to be nominally 1540 m/s), $F_t$ is the frequency of the incident beam and θ is the angle of beam incidence to the flow direction.

The turbulence is characterized by the spectral broadening which is normally seen in the presence of high flow velocity at the branching of a vessel or in small-diameter vessels. Spectral broadening can be estimated by estimating the bandwidth of the spectrum, also referred to as the spectral width. Turbulence is characterized by estimating the spectral width and therefore extracting both an upper and a lower trace of the envelope of the spectrogram. In an implementation of the present invention, the turbulence was estimated by using the area between the upper and lower spectral traces as a proportion of the area under the upper spectral trace as described by FIG. 10. FIG. 10 illustrates the computation steps involved and an illustration of a traced Doppler spectrogram is shown in FIG. 11. This criterion has the added advantage of placing the three arteries, the common, internal and external carotid, on an equal footing with respect to their peaks. It negates the effect of peak height on the estimate of spectral width. If only the width between the upper and lower envelope traces is used, this can lead to erroneous estimates owing to the external and common carotid having higher peaks than the internal carotid. Accordingly, turbulence is estimated by:

$$\text{Turbulence Criterion} = \frac{\text{Area Under Upper Trace} - \text{Area Under Lower Trace}}{\text{Area Under Upper Trace}}$$

The concluding determinations of the method of FIG. 9 are to report the finding of the carotid bifurcation point (92), indication of stenosis (90), or a normal carotid (96) to the user. These determinations are made by comparing the turbulence estimate of spectral width SW from step 84 and the PSV estimate from step 88 to a turbulence threshold $T_s$ and a velocity threshold $T_p$ in comparison steps 98*a*, 98*b*, and 98*c*. A nominal velocity threshold $T_p$ is 125 cm/sec, and a nominal turbulence criteria is 0.5. The results of these comparisons are then presented to the user on the display screen.

In summary, an implementation of the present invention provides a method for detecting and characterizing the segments of interest in a carotid artery. The inventive technique makes use of the two dimensional array Doppler probe described above and the method of vessel localization previously described, together with Doppler angle estimation for detecting a stenosis and estimating its severity. Major elements of the invention include computing the turbulence at various points in the carotid structure and characterizing turbulence with differentiated degrees of stenosis; combining the estimates of turbulence and PSV to identify the segments of interest in a carotid artery; and combining the turbulence and PSV estimates to automatically characterize the stenosis of vessel segments in terms of the degree of stenosis.

What is claimed is:

1. A Doppler ultrasound system for diagnosis of a carotid artery comprising:

a probe that comprises a two dimensional non-phased transducer array of ultrasound transducer elements arranged in rows and columns of transducer elements, the transducer elements further being canted at a Doppler angle away from orthogonal to the carotid artery when the probe is disposed over the carotid artery, the transducer elements disposed in an overlying layer of transducer lens material;

a beamformer coupled to the transducer elements of the non-phased transducer array and adapted to (i) independently actuate each transducer element, in a firing sequence of the transducer elements, to transmit pulses into a body in a pulsed wave mode and sequentially cover a range of depths and (ii) to receive Doppler signals independently from beneath each transducer element in response to the transmitted pulses, wherein the pulse wave mode provides depth resolution of the received Doppler signals;

a Doppler processor, coupled to the beamformer and responsive to the received Doppler signals for producing Doppler values for each transducer element;

a spectral Doppler processor, responsive to the Doppler values for producing a spectral Doppler profile;

a peak systolic velocity (PSV) estimator responsive to the Doppler values, which produce estimates of peak systolic velocity;

a turbulence estimator, responsive to the spectral Doppler profile, for producing estimates of flow turbulence; and a stenosis detector for producing an indication of stenosis as a function of (i) peak systolic velocity estimates and (ii) turbulence estimates.

2. The Doppler ultrasound system of claim 1, wherein the turbulence estimator further comprises an estimator for producing estimates of flow turbulence which are related to broadening of the spectral Doppler profile.

3. The Doppler ultrasound system of claim 2, wherein the stenosis detector is further operable to distinguish a carotid bifurcation from a carotid stenosis.

4. The Doppler ultrasound system of claim 3, wherein the stenosis detector distinguishes the carotid bifurcation by a normal peak systolic velocity of 125 cm/s or less and high turbulence, and distinguishes the stenosis by a high peak velocity of 125 cm/s or greater and high turbulence.

5. The Doppler ultrasound system of claim 1, wherein the spectral Doppler profile further comprises spectrogram; and wherein the spectral Doppler processor is still further configured for extracting an envelope of the spectrogram.

6. The Doppler ultrasound system of claim 5, wherein the spectral Doppler processor is still further configured for extracting an upper trace of the spectrogram and a lower trace of the spectrogram.

7. The Doppler ultrasound system of claim 6, wherein the turbulence estimator is responsive to the extraction of the upper and lower traces of the spectrogram to estimate turbulence by using an area of the spectrogram between the upper and lower traces in proportion to an area of the spectrogram under the upper trace.

8. The Doppler ultrasound system of claim 1, further comprising a vessel localization processor, responsive to the Doppler values for each transducer element and their spatial relationship to a carotid artery for producing a carotid artery vessel map.

9. The Doppler ultrasound system of claim 8, further comprising a Doppler angle estimator, responsive to the carotid artery vessel map, for estimating a Doppler angle.

10. The Doppler ultrasound system of claim 9, wherein the Doppler values produced by the Doppler processor further comprises velocity values, and wherein the PSV estimator produces estimates of the peak systolic velocity from (i) the estimated Doppler angle and (ii) a maximum value of the velocity values.

11. The Doppler ultrasound system of claim 10, wherein the maximum value of the velocity values is computed from the spectral Doppler profile.

12. The Doppler ultrasound system of claim 1, wherein the spectral Doppler profile is not displayed by the non-imaging Doppler ultrasound system.

13. The Doppler ultrasound system of claim 1, wherein the indication of stenosis further comprises an estimate of a degree of stenosis ranging from (i) normal to (ii) total occlusion.

14. The Doppler ultrasound system of claim 1, wherein the Doppler ultrasound system is configured to operate in a probe placement mode, comprising the steps of:

activating a subset of the ultrasound transducer elements and acquiring a Doppler spectrum from the subset of Doppler ultrasound elements;

computing a sum-plot integration of Doppler power in a selected frequency range; and identifying a transducer element in the subset of ultrasound transducer elements that is directly above a vessel from the magnitude of sum-plot values.

15. The Doppler ultrasound system of claim 14, wherein the probe further comprises at least one indicator providing an indication of a direction to adjust the probe or an indication that the probe is correctly positioned over a carotid bifurcation.

16. The Doppler ultrasound system of claim 14, wherein the Doppler ultrasound system further configured to operate in a vessel mapping mode, comprising the step of producing a grid-like map of the location and position of the carotid artery beneath each element of the probe.

17. The Doppler ultrasound system of claim 1, wherein the transducer elements are at least 3 mm by 3 mm in size.

18. A method for diagnosis of stenosis in a carotid artery comprising the steps of:

determining placement of a Doppler ultrasound probe comprising a two-dimensional array of non-phasing ultrasound transducer elements based on indications from the probe;

independently actuate each transducer element of the two-dimensional array of non-phasing ultrasound transducer elements, in a firing sequence of the transducer elements, to transmit pulses into a body in a pulsed wave mode and sequentially cover a range of depths receive Doppler signals independently from beneath each transducer element in response to the transmitted pulses, wherein the pulse wave mode provides depth resolution of the received Doppler signals;

producing Doppler values for each transducer element;

producing a spectral Doppler profile from the Doppler values;

producing estimates of peak systolic velocity from the Doppler signals;

producing estimates of flow turbulence from the Doppler signals; and producing an indication of stenosis as a function of (i) peak systolic velocity estimates and (ii) turbulence estimates.

19. The method of claim 18, wherein the Doppler profile comprises a spectrogram and producing a turbulence estimate comprises:

extracting an upper and a lower trace from the spectrogram and;

calculating turbulence as an area of the spectrogram between the upper and lower traces in proportion to an area of the spectrogram under the upper trace.

* * * * *